(12) United States Patent
Ferguson

(10) Patent No.: US 11,073,478 B2
(45) Date of Patent: Jul. 27, 2021

(54) FLUID MONITORING SYSTEM AND METHOD

(71) Applicant: Brenton Ferguson, San Antonio, TX (US)

(72) Inventor: Brenton Ferguson, San Antonio, TX (US)

( * ) Notice: Subject to any disclaimer, the term of this patent is extended or adjusted under 35 U.S.C. 154(b) by 0 days.

(21) Appl. No.: 16/639,383

(22) PCT Filed: Aug. 14, 2018

(86) PCT No.: PCT/US2018/046778
§ 371 (c)(1),
(2) Date: Feb. 14, 2020

(87) PCT Pub. No.: WO2019/036518
PCT Pub. Date: Feb. 21, 2019

(65) Prior Publication Data
US 2020/0256795 A1    Aug. 13, 2020

Related U.S. Application Data

(60) Provisional application No. 62/545,023, filed on Aug. 14, 2017.

(51) Int. Cl.
*G01N 21/66* (2006.01)
*G01N 21/31* (2006.01)
*G01N 21/85* (2006.01)
*G01N 33/18* (2006.01)

(52) U.S. Cl.
CPC ............. *G01N 21/66* (2013.01); *G01N 21/31* (2013.01); *G01N 21/85* (2013.01); *G01N 33/18* (2013.01)

(58) Field of Classification Search
CPC ........ G01N 21/66; G01N 21/31; G01N 33/18; G01N 21/05; G01N 21/63; G01N 21/645; G01N 21/6482; G01N 21/6471; G01N 2201/062; G01N 2201/0635; G01N 2201/064
USPC ................... 250/453, 436, 435, 493.1, 494.1
See application file for complete search history.

(56) References Cited

U.S. PATENT DOCUMENTS

| | | | |
|---|---|---|---|
| 2004/0179194 A1* | 9/2004 | Schmilovitch | G01N 21/3577 356/244 |
| 2006/0173253 A1* | 8/2006 | Ganapathy | A61B 5/1468 600/310 |
| 2007/0138401 A1* | 6/2007 | Tokhtuev | G01J 3/36 250/373 |
| 2018/0246035 A1* | 8/2018 | Hasegawa | G01N 21/64 |
| 2019/0100718 A1* | 4/2019 | Estes | C12H 1/165 |

* cited by examiner

*Primary Examiner* — Nicole M Ipppolito
(74) *Attorney, Agent, or Firm* — Donn K. Harms

(57) ABSTRACT

A device and method for determining substances within a fluid stream through the employment of light projected therethrough or emitted by the substances energized in the fluid stream. The device features a fluid chamber through which light, at known wavelengths, is projected through the fluid stream to a light sensor. The substances in the fluid stream are determinable by ascertaining which respective light wavelengths emitted by the light emitter do not contact the light sensor because they are absorbed by respective substances in the fluid stream. Alternatively, the substances in the fluid stream can be energized to emit light in wavelengths which can be ascertained as emitted by individual substances.

11 Claims, 3 Drawing Sheets

FLUID MONITORING SYSTEM AND METHOD

This application claims priority to U.S. Provisional Patent Application Ser. No. 62/545,023 filed on Aug. 14, 2017, which is incorporated herein in its entirety by this reference thereto.

FIELD OF THE INVENTION

The disclosed device relates to the monitoring of fluids. More particularly, the device relates to a device and method employing spectral monitoring such as using spectroscopy for the continuous monitoring of the contents and quality of a fluid through the employment of spectral monitoring of the fluid flowing through a housing of the device herein.

BACKGROUND OF THE INVENTION

The inspection and ongoing monitoring is a constant task for many industries, government municipalities, homeowners, and hobbyists and the like. For example, water is a common fluid which has quality requirements which must be met. Such quality requirements can vary widely by industry or water use, and the ongoing maintenance of the proper quality of water for these differing uses is a constant and common problem. The same is true of other fluids employed in other industries such as liquid fuels.

In the field of water, the ongoing or potential use of the water can require stringent quality and cleanliness such as where water is employed for the manufacturing of food or drinks. Beer and soda bottlers, for example, have a constant and ongoing issue with the cleanliness and hardness of the water being employed. Such is easily affected by bacteria or particulate or plant growth such as algae, which forms in water. Due to the volume of products manufactured, a drop or issue with water quality can cause significant problems.

Another example is in the use of water for aquariums and fluid habitats. While such water may have allowable levels of additives and particulate and the like, each item dissolved or flowing as particulate in the water used, must be kept at designated levels to maintain a fluid habitat for fish and other water-occupying creatures, to maintain their health. Current concerns with regard to fish and water habitats for animals relate to making sure that certain elements in the water are only present at levels not harmful to the occupants. Conventionally of concern water is tested for one or a combination of possible water components or issues from a group including Ammonia Nitrite, Nitrate, Salinity/Specific Gravity, water pH, Carbonate Water Hardness, Alkalinity, Chlorine and Chloramine, Copper, Phosphate, Dissolved Oxygen, Iron and Carbon Dioxide among other things. However, testing for the presence and levels of such is currently hard to accomplish and time consuming and not well adapted for constant monitoring.

In some cases, the water or other fluid employed for a particular purpose or industry, must have constant levels of multiple additives in the water for current or anticipated use. For example, in horticulture and landscaping, the water supply may have varying requirements for fertilizer levels, mineral levels, and other additives that are employed in growing a crop, watering a park or golf course, or just maintaining a residential yard with healthy plants.

While various fluid monitoring devices exist, such devices are conventionally specialized sensors or fluid sampling devices such as reagent embossed paper, which monitor a single additive or contaminant. For example, electronic sensors are employed which have a sensor immersed in the fluid which generates an electric signal relative to the levels of a particular ingredient in the water or fluid. Also available are chemical sensors which employ test materials which have reactants positioned thereon which will change color in a visually discernable manner relative to the levels of a particular individual ingredient in the water or fluid. However, such electronic and chemical sensors and similar devices are conventionally adapted to only sense a single element or contaminant content in a fluid such as water, and therefor are not easily employed to concurrently monitor a fluid for a plurality of different contaminants, chemicals, or desirable additives. Neither are they easily changed to monitor for a different chemical or contaminant or content, since the electronic sensors are conventionally adapted to only react at a predicted electric current to a single item. Still further, because of the time for testing involved and the multiple tests required, the actual testing can have long periods therebetween where the fluid or water can become less than desirable as a chemical or other containment is not found between tests.

The device and system herein overcomes previous shortcomings and provides for an ongoing fluid monitoring of fluid such as fluid in water habitats or fluid used in food or other manufacturing. The system herein continuously monitors a moving fluid stream sample for a plurality of different contaminants, additives, particulate, or other matter present in the water or fluid. In addition to being capable of ongoing concurrent fluid monitoring for a plurality of fluid contents, the system herein is easily updated or changed to monitor for additional items present in a fluid supply, or to eliminate monitoring for one or more fluid contents and concurrently add the ability to monitor for new fluid contents or contaminants quickly.

The forgoing examples of related art of fluid monitoring, and limitations related therewith, are intended to be illustrative and not exclusive, and they do not imply any limitations on the invention described and claimed herein. Various other limitations of the related art are well known or will become apparent to those skilled in the art upon a reading and understanding of the specification herein and the accompanying drawings.

BRIEF SUMMARY OF THE INVENTION

The disclosed fluid monitoring system herein provides a device and method for employment thereof, which is a solution to the noted shortcomings of fluid quality control. The system herein through the provision of a fluid monitoring device and method which employs a spectrometer provides an ongoing real-time monitoring of fluid as well as an ongoing quality reporting of the fluid flowing through a housing. In one mode of the system herein, a light-emitting component positioned within the housing on a first side of a central fluid chamber. On the opposite side of the central fluid chamber, in a sensing chamber, is housed a light sensing component which is adapted to receive light transmitted through the fluid in the central fluid chamber and communicate such to a computing device operatively engaged which employs software configured to the task of receiving the electronic signals from the light sensing component and correlating such to the content of the fluid. The centrally located fluid chamber is configured to allow continuous or timed fluid flow therethrough which enters under pressure provided by a pump or the like, from a first end of the housing and flows to an exit at an opposite end of the housing.

The volume of the fluid in a light pathway in the fluid chamber can be processed to determine the atoms or molecules of substances within the volume of fluid sample using lightwave absorption by the contents therein, or using lightwave emission from the materials within the fluid sample. Both modes of testing use the electronic signals correlating to lightwaves received by a CCD or other electronic light sensing components which generates electric signals. By substances herein is meant any substance be it dissolved or a particulate within the fluid stream which will absorb light waves in a known frequency or spectrum, or will emit light in a known frequency or spectrum when energized by a magnetic filed, electricity, or UV light.

In one preferred mode herein, a light emitter is energized to emit light along a light pathway and through a known volume of fluid in a central fluid chamber. Atoms and molecules of substances in the fluid sample absorb lightwaves at known light frequencies and therefor subtract those from the light received by the sensors on the opposite side of the sampling chamber. By discerning the original frequencies of lightwaves generated and communicated into the chamber with fluid, and comparing those to the electric signals from the light sensing CCD or other device, missing lightwaves at individual frequencies known to correlate to atoms, molecules forming substances in the fluid can be determined, and the material within the fluid sample can be ascertained with great accuracy. The system can take the step of making multiple light transmissions and readings from the light sensing component and averaging the amounts of the contents of the fluid so as to make sure that a single sample is not calculated in error.

As for the light emission sampling, the previously stated light source may be turned off and the fluid sample will be excited either by electrodes therein, or by a UV light source. In this emission sampling mode, the atoms and molecules forming substances within the fluid sample in the light pathway, will emit their own respective lightwaves at a known spectrum or frequency, which are communicated along the light path to a sensor such as a CCD, and the electric signals correlating to each sensed lightwave frequency so emitted can be discerned. The atoms or molecules of substances in the fluid can thus be determined by the electric signals generated by the CCD which the software on the system is configured to correlate to known electric signals for individual substances in an electronic database of such either using an absorption mode or an emission mode, or both.

In both modes of light based sampling of a volume of fluid in the central fluid chamber, the individual specific wavelengths of light are passed through a diffraction component such as a prism or diffraction grid. The diffraction component segments and arranges the transmitted light in such a way to contact the light sensor to better capture the spectral data and generate electric signals correlating to such.

The fluid chamber has light transmitting portions inside walls on opposite sides. A first sidewall is situated in between the light-emitting component. A second sidewall is positioned on the opposite side of the fluid chamber adjacent the light sensing component. Electrodes may be situated within the fluid chamber should the light emission mode of sampling be employed either alone or in combination with the absorption mode.

In operation, as fluid is in or passing through the fluid chamber, light waves emitted from the light emitter communicate through the first sidewall and through the fluid within the fluid chamber, and exit through the second sidewall into the receiving chamber of the housing where the light sensing component is located.

The light emitter may employ one or a plurality of light emitters, such as LEDs which may individually or in combination, generate a light transmission at one or a plurality of frequencies, which communicates through the first sidewall, fluid, and second sidewall, and is received in real time by the light sensors of the light sensing component.

The light sensing component, such as a Charged Coupled Device (CCD) receives light transmitted through the fluid and generates an electric signal based on one or a plurality of light frequencies which are received by one or a plurality of such light sensors operatively engaged to electric power and a computing device having software or firmware thereon. One, or a plurality of differing electric signals are generated and transmitted from the light sensors such as from one or more CCDs. Each such electric signal correlates to the strength and frequency of light waves the sensor received.

In operation, each of the electric signals which correlate to the wavelengths and strength of a light frequency of light being monitored, are communicated to a computing device having software running in electronic memory configured to the task of receiving and recognizing each of the electronic signals and generating an identity of one or a plurality of contents in the fluid.

The software correlates the received electric signals from the senor to stored electronic signals held in a database in electronic memory, where each stored electronic signal correlates to an atom or compound or molecule. As a brief explanation, in every atom/compound there is a discernable outer electron shell. Based on the attractive forces caused by internal components (combination of protons and neutrons) of the atom/compound, the distance of the gap of each of these outer electron shells for each such atom/compound is finite and distinct, and corresponds to a specific light wavelength. Each light wavelength corresponds with the exact distance of the gap between the last stable and outer electron shells. Thus, for each atom/compound or molecule this specific light wavelength when discerned, can be used to identify the atom/compound like a digital finger print or electric signal corresponding to the specific light wavelength of each atom/compound or molecule.

The way identification is done is by measuring the distance of the outer shells of a plurality of such atom/compounds. When a sample of an atom/compound is hit with a known light source it absorbs the corresponding bands from the full spectrum of the light source. By measuring the difference at those specific bands, one can measure the concentration and presence of a particular atom/compound using Beere's law.

Inversely using the emission mode of the system, if the electrons in the atoms or molecules in the fluid sample are excited by one or numerous means, such as with UV spectrum light or by adding electricity or a magnetic field to the sample, light emitting plasma is created. The energy added to the atom/compound makes the electrons thereof jump to an expanded or outer shell but such are highly unstable. Being unstable, the electrons then jump back to the size of the previous shell. In this expansion and contraction process a photon of light is emitted at the same wavelength that corresponds with the individual absorption band associated with each atom/compound noted earlier. The presence and concentration of an atom/compound thus can be calculated by measuring the wavelength and level or amount of light output during the contraction of the energized shell, based on the same Beere's law. Thereafter, the light reception component such as a CCD will generate electric signals corresponding to the emitted light from the excited sample which as noted above can be employed through comparison with a database of known electric signals correlating to substances, to determine the contents of the sampled fluid volume.

It should be noted that either one or both of the absorption and emission testing can be employed. When used together the system can alternate full spectrum light for determining absorption and UV light or current generation in the sample for determining light emission, and compare or average the results over a time period sufficient to sample a plurality of volumes of the fluid in the central fluid chamber.

In the system, a database of such digital finger prints, each of which correlates an electronic signal transmitted by a light sensor which is associated with a specific light wavelength known to correlate to an individual atom/compound or molecule, is formed through testing. The set of such electronic signals which the light sensor may transmit, with each correlating to a wavelength of an individual atom/compound, is held in an electronic database accessible by the system. Thereafter, comparison software running in electronic memory and on a computer, which is configured to receive electric signals from the light sensor or CCD or the like herein, and compare the electric signal correlating to a light wavelength captured by the CCD or other light sensor, to those held in the database is employed. The software identifies the electric signal from the sensor and correlates that to a wavelength of light. Thereafter it matches the discerned light wavelength to those in the database where each relates to matching specific atom/compounds.

Employing the computing processor, the software thus ascertains the exact frequency of light waves being received by the light sensors, and their respective relative strengths, based on the electric signal therefrom, and ascertains the percent of one or a plurality of atoms/compounds within the fluid in the fluid chamber by volume.

In operation in absorption mode, the light generated preferably in a full spectrum, being communicated from the light emitter through the fluid, thus allows for discerning of the atoms or individual molecules of differing materials mixed with the liquid within contents of the fluid chamber. The light waves from the light emitters, in the manner noted above, interact with the bonds in the molecules of the liquid, dissolved solids, particulate, bacteria, and other material contained in the fluid within the fluid chamber. The light not absorbed which communicates through the fluid from the light emitters to the sensors will resonate at the particular pre-identified frequencies so as to identify the differing molecules in the fluid from a "spectral fingerprint."

Held in a database, in electronic memory, is a listing of the molecules of interest and their respective spectral fingerprint when illuminated by light waves at a particular frequency. Using the electric signals from the light sensors in the sensing component such as a CCD which are communicated to the computing device, a comparison may be accomplished with the various spectral fingerprints held in electronic memory, to ascertain, with great accuracy, the relative contents within the fluid chamber, be it pure fluid or fluid with additives or contaminants.

Thereafter, with the knowledge of the contents of the fluid chamber derived using the device herein, the user may adapt the fluid with filters, additives, chemicals, etc. to make the fluid conform to the desired characteristics. The arrival at a fluid mixture or flow with the desired characteristics can be ascertained by the device using the light emitted and received by the sensors which can generate the relative signals to the computing device to ascertain with spectral fingerprints that the mixture or content in the fluid chamber, and flowing therethrough, meets the user's requirements for such.

For example, where pure water is desired for food or the like, the water is continuously measured for any contaminants therein, by the communication of full spectrum or if desired partial spectrum light from the emitters at the appropriate frequency. The generated light will pass through the water flowing in the fluid chamber in real time. The light sensors configured to receive the light waves transmitted through the fluid and not absorbed by material in the fluid, at the appropriate frequency from the light emitters, can on an ongoing basis generate electric signals relative to the received lightwave frequencies. This, as noted, may be employed to derive an ongoing spectral fingerprint of the water purity. In this fashion the water flowing through the device can be continually monitored for purity. Such continuous measurements could be handled by ongoing measurements in real time, or continuous sampling using individual measurements taken over determined time durations. Alternatively, the emission mode may be employed over time to determine purity and/or can be used in combination with the absorption mode of the system for self-checking the results and/or enhanced accuracy.

As noted above, if the fluid such as water is desirable with other materials therein for other purposes such as landscaping or laundry, the fluid passing through the fluid chamber can be continually monitored by the communicated light therethrough to ascertain that the fluid has the appropriate spectral fingerprints of the desired molecules or material within the fluid, at the desired ratio relative to the volume of fluid in the fluid chamber. In this fashion, the device could monitor fertilizer bearing water for landscaping, or water with clothes conditioner therein for laundry. As may be discerned, any fluid for any purpose may be monitored as it flows through the fluid chamber of the housing of the device herein.

With respect to the above description, before explaining at least one preferred embodiment of the herein disclosed fluid monitoring device herein invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art upon reading this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed fluid monitoring system. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising." Thus, use of the term "comprising" indicates that the listed elements are required or mandatory, but that other elements are optional and may or may not be present. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

It is an object of the present invention to provide a highly efficient and easily employed fluid monitoring device which provides a user ongoing real time information concerning fluid purity and contents.

It is an additional object of this invention to provide such a fluid monitoring device and method which is compact, easily engaged with any fluid circuit, and easily upgraded and adjusted for the monitoring of differing fluids and differing contents.

These and other objects, features, and advantages of the present fluid monitoring device and method invention, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF THE DRAWINGS

The accompanying drawings, which are incorporated herein and form a part of the specification, illustrate some, but not the only or exclusive examples of embodiments and/or features of the disclosed device and system. It is intended that the embodiments and figures disclosed herein are to be considered illustrative of the invention herein, rather than limiting in any fashion. In the drawings.

DETAILED DESCRIPTION OF THE PREFERRED EMBODIMENTS OF THE INVENTION

Figure 1:
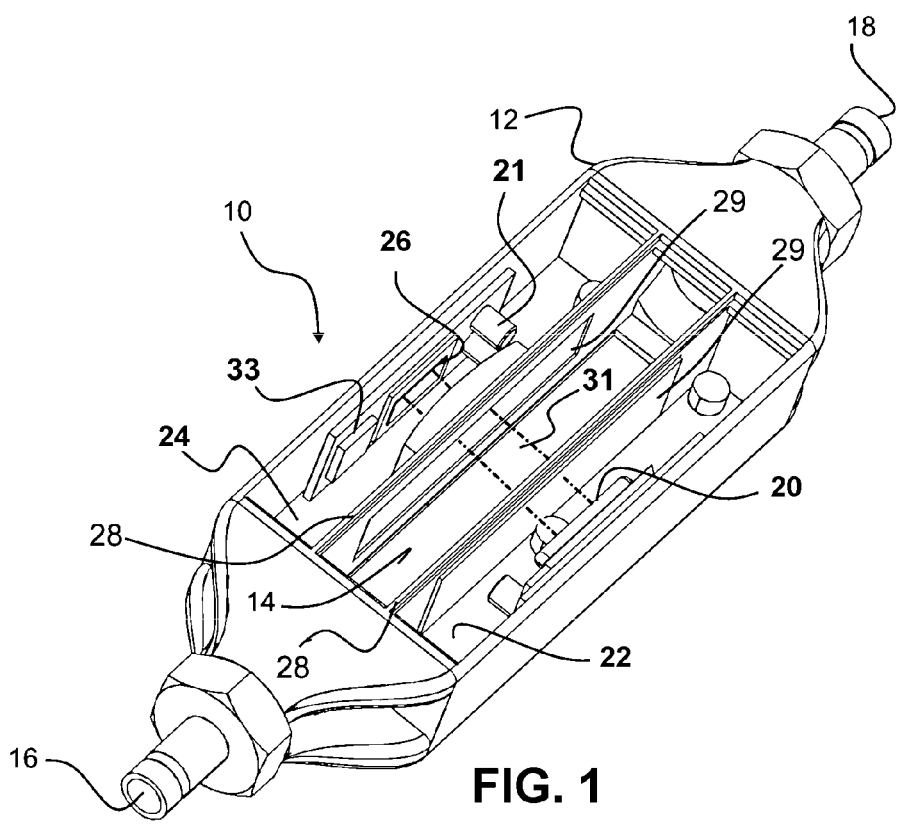
FIG. 1 depicts a first perspective view of the device herein showing the light chamber adjacent a fluid chamber having light passing portions which allow communication of light along a light pathway from the light chamber, through the fluid chamber, to the receiving chamber.

The device 10 and system herein disclosed and described in FIGS. 1-4 provide a solution to the shortcomings in prior art of fluid monitoring. The device 10 enabling the system herein, has a housing 12 having a fluid chamber 14 running therethrough in communication with an inlet 16 at a first end of the housing 12 and an outlet 18 at a second end of the housing 12.

A light-emitting component or light emitter 20 is positioned within a light chamber 22 located on a first side of the fluid chamber 14. As noted, the light emitter 20 may be an LED or other light emitting device and may emit full spectrum light or light in known frequencies or wavelengths to allow absorption thereof within the fluid chamber 14, or it may be UV light where light emission is generated by the materials in the fluid running through the volume in the fluid chamber 14 in the desired mode for measurement thereof. With either absorption or emission, the light sensor or light sensing component 26 will be caused to generate an electric signal correlating to the light frequency or wavelength sensed as contacting the surface of the light sensor 26, as well as a higher or lower voltage or other readable electric signal strength relative to an amount of each light wavelength contacting it. Absorbed light from substances in the fluid will be missing from such light wavelengths in the absorption mode and will be present in received light wavelengths emitted by substances in the emission mode.

Figure 4:
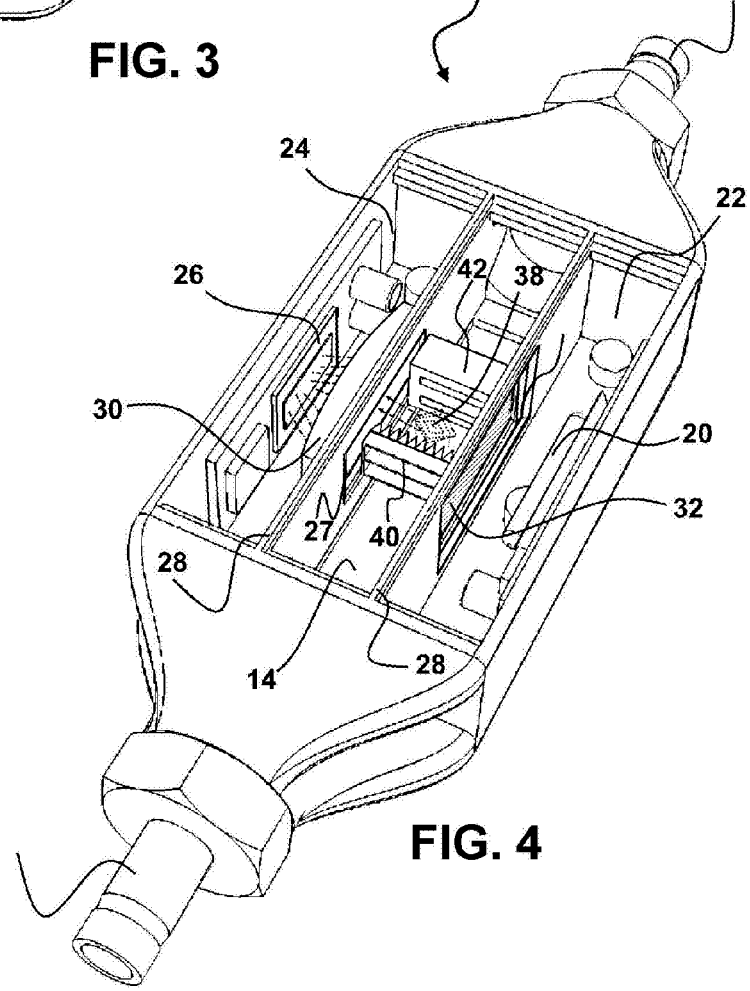
FIG. 4 depicts a mode of the device having a cathode and anode within the fluid passage to impart electric current to the fluid for operation in an emission mode of the device or combination emission and absorption mode.

Thus, using either the noted light absorption mode or light emission mode or both, the atoms or molecules forming a respective substance within the volume of fluid, within the fluid chamber 14 at any instant in time, can be determined by the missing wavelengths from the communicated light spectrum from the light emitter 20 or from the discerned received light wavelengths from a generated emission 38 (FIG. 4).

On the opposite side of the fluid chamber 14 in the sensing chamber 24 is positioned a light sensor or light sensing component 26. As noted, the fluid chamber 14 is configured to allow a known volume of fluid to flow through it in a time duration where the fluid enters from the inlet 16 and exits at the outlet 18 and passes through an area of the fluid chamber having a formed light pathway 31.

In a simple mode of the device 10 herein, light passing portions 27 of side walls 28 may be positioned aligned on opposing sides of an area of the fluid chamber 14, between the light chamber 22 and light sensing chamber 24. In use, as fluid is in or passing through the area of the light pathway 31 in the fluid chamber 14, light waves in the spectrum emitted from the light emitter 20, will communicate through a first of the light passing portions 27 of sidewalls 28, and then through the fluid within the fluid chamber 14, and through the second light passing portion 27 of the opposing sidewall 28 where it then passes into the sensing chamber 24 of the housing 12. By light passing portions is meant a portion of the sidewall 28 is formed of a material which will pass the spectrum or wavelength of light therethrough which is intended to communicate through the fluid to the light sensor 28 in determining the contents in the fluid volume in the fluid chamber 14. This may be polymeric material, glass, or other material as would occur to those skilled in the art for light passage.

In the absorption mode of the device 10 such as in FIG. 4, the light received by the light sensing component 26 within the sensing chamber 24 includes light emissions from the light emitter 20 in a full or known spectrum, minus the wavelengths of light at the frequencies absorbed by atoms and molecules of one or more substances in the fluid. This reception of transmitted light minus the wavelengths absorbed, causes the generation of an electric signal by the light sensor 26, based on the actual light wavelengths or frequencies which are received by one or a plurality of light sensing components 26 located in the sensing chamber 24. By full spectrum light is meant the electromagnetic spectrum from infrared to near-ultraviolet, or portions thereof which are calculated to have wavelengths to be absorbed by the atoms or molecules forming substances in the fluid for which the device 10 is to be employed for testing.

As noted, thereafter, each of the electric signals from light sensor 26 or sensors correlating to the wavelengths and strength of a light frequencies sensed, are operatively communicated to a computing device using wired or wireless communication thereto such as with a WiFi or Bluetooth transmitter 21. It should be noted the device 10 is operatively connected to a power source such as a battery (not shown) or power supply or the like both of which are well known.

The computing device may be onboard as a processing chip 33 with electronic memory, or may be in operative wired or wireless communication with the device 10 in a conventional wired or wireless connection. The computing device has software running in memory and a processor which employs the software operating to discern the electric signals concerning the frequency of light being received by the light sensors 26, and their respective relative strengths, and to compare such to a database of electric signals where each correlates to a substance which can then be ascertain as present in the fluid chamber 14 by volume.

The system is easily adapted to sense differing substances and contents of the fluid in the fluid chamber 14, by adapting the wavelength of the light emitted by the light emitter 20, such that wavelengths light generated and passing through the fluid, will be absorbed and cause the generation of an electric signal by a light sensing component 26, which receives the original spectrum minus the wavelength or spectrum absorbed by the substance. The missing wavelengths of absorbed light correlate to the one or plurality of substances sensed in the fluid contents of the fluid chamber 14. Currently, full spectrum light generated by the light-emitting component provides light transmission through the fluid sample which is well adapted to discern substances such as solids and dissolved content using the absorption mode.

As noted, the frequency or wavelength of light missing in the sensed light received by the sensing component 26, when compared to that transmitted from the light emitter 20, causes electronic signals to be generated which can be correlated to the contents of the fluid from a database of materials correlated to respective wavelengths they absorb. As noted above, spectral fingerprints for different materials based on the light wavelengths absorbed thereby at one or more light frequencies or spectrum fingerprints, can be developed and stored in electronic memory in a database of electronic spectral fingerprints correlating to atoms and molecules forming respective substances. This database is later employed using software operating for comparison of light wavelengths or frequencies in the sensed electric signals form the light sensor 26, to ascertain differing substances within the fluid in the fluid chamber 14.

Figure 2:
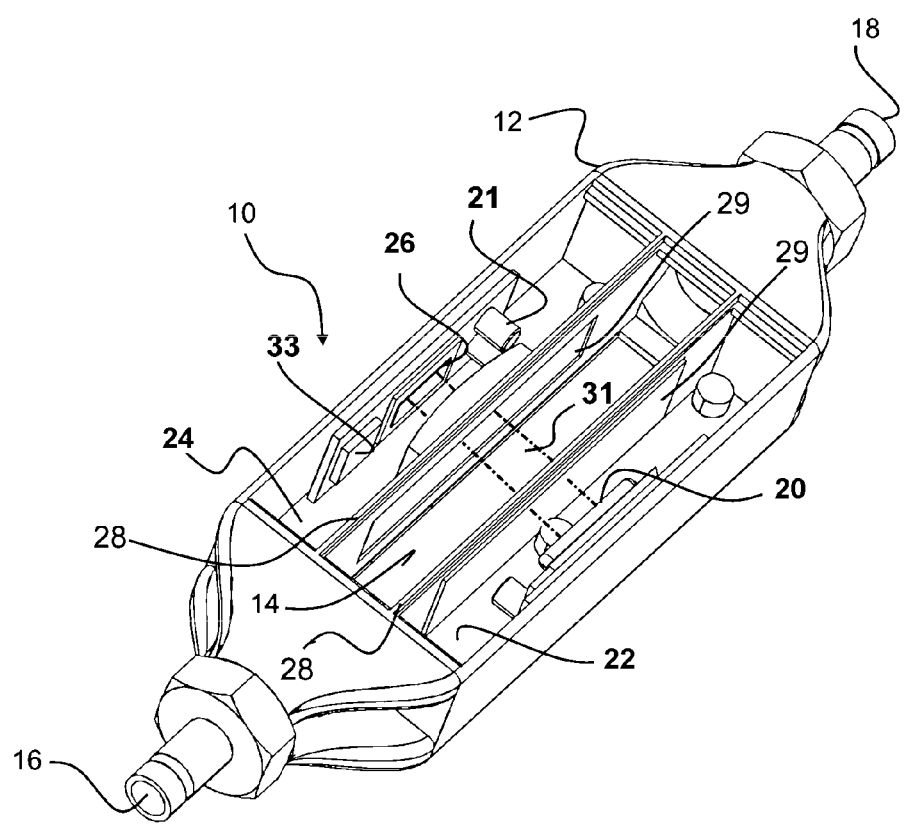
FIG. 2 is a second perspective view of the device of FIG. 1.
Figure 3:
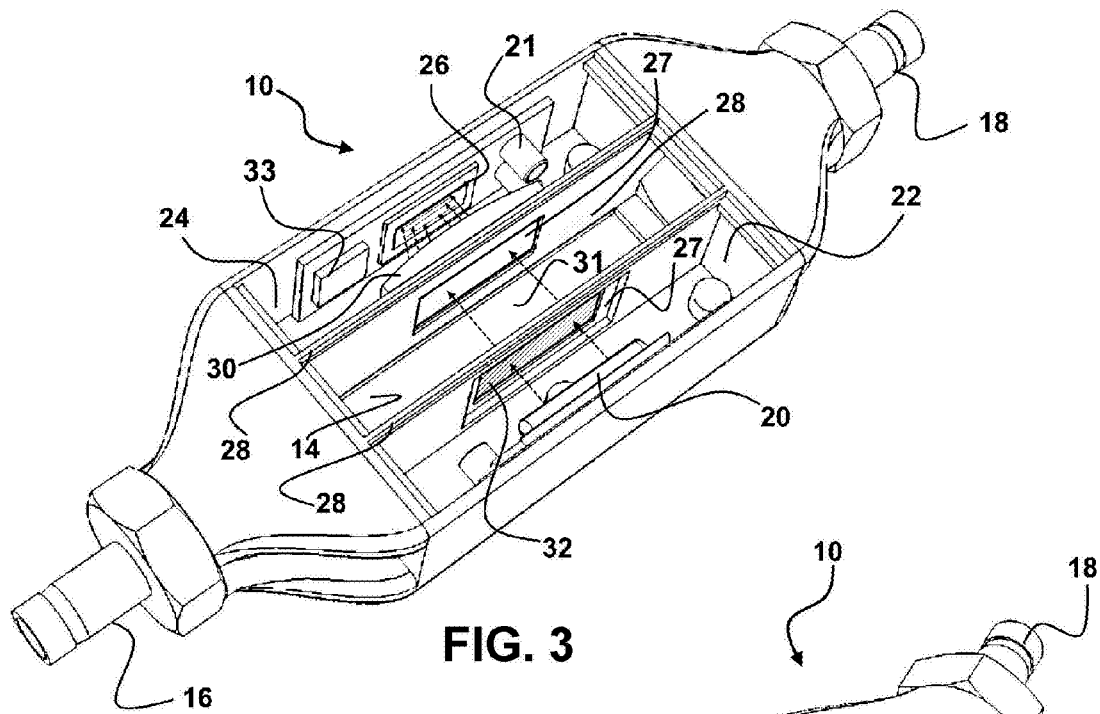
FIG. 3 shows another view of the device showing the preferred diffraction component with a slit filter positioned in the pathway for light through the sampled volume of fluid.

Shown in FIG. 3, is another view of the device 10 such as in FIGS. 1-2, showing the sidewalls having a preferred diffraction component or diffraction grating 30 and having a slit filter 32 positioned aligned positions in the sidewalls 28. In such positions in the sidewalls 28, diffraction grating 30 splits and diffracts incoming light into several beams traveling in different directions and locations or rows upon the surface of the light sensor 26. Such renders the sensing of the light sensor 26 either in the absorption mode or emission mode of the device 10 herein, more accurate in determining the wavelengths of light contacting the light sensor 26 which thus generates more accurate electric signals.

The slit filter 32 is also preferred as experimentation has shown that the diffraction of light from the light emitter 20 which occurs communication through the slit filter 32, which then travels through the fluid sample and through the diffraction grating 30 has shown to yield more accurate results for the device 10.

Finally, shown in FIG. 4, is a mode of the device 10 herein, having an a cathode 40 and anode 42 separated by a gap therebetween. The gap is positioned within the fluid chamber 14 in a location aligned with a light pathway 31 which extends from the light emitter 20, through the aligned light passing portions 27 of the opposing sidewalls 28 of the fluid chamber 14, and to the light sensor 26. The cathode 40 and anode 42 are operatively connected to an electric power source such as a battery or AC power. The anode 42 and cathode 40 when placed in an energized configuration in a connection to the electric power source impart electric power running therebetween and thereby generate one or a plurality of light emissions 38 which are emitted by the material in the fluid formed of differing atoms and molecules forming substances in the fluid, which are energized within the gap between the cathode 40 and anode 42. As noted above, this light emission 38 can also be initiated by a light emitter 20 which projects UV along the light pathway 31 through the fluid in the fluid chamber 14 to the light sensor 26 whereby the UV light provides the means to energize the material within the fluid stream.

The light emissions 38 generated from the energized material in the fluid stream which travels to the light sensor 26 along the pathway 31 is used in the emission mode of the device 10. As also noted, the device 10 as shown in FIG. 4, could take both emission and absorption measurements alternately by energizing the light emitter 20 and then the cathode 40 and anode 42 or UV light from the light emitter 20, and employ software running in electronic memory of a computing device to compare the results to test for accuracy, or to average the results over a time period of individual sequential light measurements, for better accuracy. This is because the fluid is moving through the volume within the light pathway 31 and may have unequal quantities of undesirable materials therein in different amounts within the fluid chamber 14.

While all of the fundamental characteristics and features of the fluid monitoring system have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications, variations and substitutions are included within the scope of the invention as defined by the following claims.

What is claimed is:

1. An apparatus for discerning substances in a fluid stream, comprising:
   a housing, said housing having a fluid chamber defined between a first surface of a first sidewall opposite a first surface of a second sidewall, said fluid chamber communicating between an inlet for a fluid stream and an outlet for said fluid stream;
   said first sidewall having a second surface on an opposite side from said first surface and said second sidewall having a second surface on an opposite side from said first surface thereof;

a first light passing portion formed in said first sidewall in an aligned position across an area of said fluid chamber from a second light passing portion formed in said second sidewall;

a light emitter positioned adjacent said second surface of said first sidewall, said light emitter emitting light in a range of wavelengths;

a light sensor positioned adjacent said second surface of said second sidewall;

a light pathway running from said light emitter through said first light passing portion, across said area of said fluid chamber, and through said second light passing portion, to said light sensor;

said light sensor producing an electronic signal correlating to respective wavelengths of light from said range of wavelengths which contact said light sensor; and substances in said fluid stream in said area of said fluid chamber being identifiable by discerning said respective said wavelengths of light from said range of wavelengths emitted by said light emitter which are absorbed by said substances and thereby rendered absent from said range of wavelengths which contact said light sensor.

2. The apparatus for discerning substances in a fluid stream, of claim 1, additionally comprising:

a computing component operatively engaged with electronic memory;

a database held in electronic memory associating said respective wavelengths of light from said range of wavelengths emitted by said light emitter, which are absorbed by individual respective substances;

software running on said computing component operating to the task of discerning which respective wavelengths of light from said wavelengths emitted by said light emitter, are not contacting said light sensor, by discerning said electronic signals from said light sensor which correlate to respective wavelengths of light from said range of wavelengths which are contacting said light sensor; and software running on said computing component operating to match determined respective wavelengths of light from said wavelengths emitted by said light emitter not contacting said light sensor with respective substances in said database in said electronic memory which absorb said respective wavelengths of light not contacting said light sensor, whereby respective said substances in said fluid stream are identified by said respective said wavelengths of light from those emitted by said light emitter said respective substances absorb.

3. The apparatus for discerning substances in a fluid stream, of claim 2, additionally comprising:

a slit filter positioned between said light emitter and said first light passing portion.

4. The apparatus for discerning substances in a fluid stream, of claim 3, additionally comprising:

a diffraction grating positioned between said light sensor and said second light passing portion.

5. The apparatus for discerning substances in a fluid stream, of claim 2, additionally comprising:

a diffraction grating positioned between said light sensor and said second light passing portion.

6. The apparatus for discerning substances in a fluid stream, of claim 1, additionally comprising:

a slit filter positioned between said light emitter and said first light passing portion.

7. The apparatus for discerning substances in a fluid stream, of claim 6, additionally comprising:

a diffraction grating positioned between said light sensor and said second light passing portion.

8. The apparatus for discerning substances in a fluid stream, of claim 1, additionally comprising:

a diffraction grating positioned between said light sensor and said second light passing portion.

9. The apparatus for discerning substances in a fluid stream, of claim 1, additionally comprising:

a UV light emitter communicating UV light along said light pathway to said light sensor;

said UV light energizing respective said substances located in said fluid stream to emit light in a respective emission light wavelength;

said light sensor producing an electronic signal correlating to respective light at said emission light wavelengths which contact said light sensor; and substances in said fluid stream in said area of said fluid chamber being identifiable by matching each respective said electronic signal correlating to a respective said emission light wavelength, with an electronic signal pre associated with a said substance known to emit light at said respective said emission light wavelength.

10. The apparatus for discerning substances in a fluid stream, of claim 1, additionally comprising:

a cathode positioned on a first side of said area of said fluid chamber in-between said first light passing portion and said second light passing portion;

an anode positioned on a second side of said area of said fluid chamber opposite said first side;

said cathode and anode having an energized state upon communication of an electric current thereto;

said energized state of said cathode and anode energizing respective said substances located in said fluid stream therebetween, to emit light in a respective emission light wavelength;

said light sensor producing an electronic signal correlating to respective light at said emission light wavelengths which contact said light sensor; and substances in said fluid stream in said area of said fluid chamber being identifiable by matching each respective said electronic signal correlating to a said emission light wavelength, with an electronic signal pre associated with a said substance known to emit light at said respective said emission light wavelength.

11. A method of identifying substances within a fluid stream employing the device of claim 1, comprising:

running a fluid stream through said fluid chamber;

energizing said light emitter to emit light in said range of wavelengths;

identifying each respective electronic signal correlating to a respective wavelength of light from said range of wavelengths of light emitted by said light emitter, which contact said light sensor;

determining missing individual wavelengths of light emitted by said light emitter which are not contacting said light sensor by ascertaining which respective wavelengths of light emitted by said light emitter are not contacting said light sensor by discerning respective said electronic signals which are not being generated by said light sensor which missing signals correlate to said missing individual wavelengths of light; and matching said missing individual wavelengths of light to substances known to absorb said missing wavelengths of light.

* * * * *